United States Patent
Wachtenberg

(10) Patent No.: US 7,404,801 B2
(45) Date of Patent: Jul. 29, 2008

(54) BLOOD PRESSURE MONITOR

(75) Inventor: Eyal Wachtenberg, Kfar Sava (IL)

(73) Assignee: Quicare Ltd., Kfar Saba (IL)

( * ) Notice: Subject to any disclaimer, the term of this patent is extended or adjusted under 35 U.S.C. 154(b) by 208 days.

(21) Appl. No.: 10/556,147

(22) PCT Filed: Apr. 1, 2004

(86) PCT No.: PCT/IL2004/000300

§ 371 (c)(1),
(2), (4) Date: Nov. 7, 2005

(87) PCT Pub. No.: WO2004/100783

PCT Pub. Date: Nov. 25, 2004

(65) Prior Publication Data

US 2006/0217617 A1   Sep. 28, 2006

(30) Foreign Application Priority Data

May 15, 2003   (IL) ............................... 155956

(51) Int. Cl.
*A61B 5/02* (2006.01)
(52) U.S. Cl. ........................ 600/495; 600/499
(58) Field of Classification Search ............... 600/490, 600/500, 503, 485, 493–496
See application file for complete search history.

(56) References Cited

U.S. PATENT DOCUMENTS

| 3,189,024 A | * | 6/1965 | Smith ............ 600/495 |
| 3,527,204 A | * | 9/1970 | Steinbeck et al. ....... 600/496 |
| 3,581,734 A | | 6/1971 | Croslin et al. |
| 4,660,567 A | * | 4/1987 | Kaneko et al. .......... 600/495 |
| 4,747,412 A | | 5/1988 | Yamaguchi |
| 4,809,700 A | * | 3/1989 | Castelli ............ 600/384 |
| 4,896,676 A | * | 1/1990 | Sasaki ............. 600/494 |
| 5,031,631 A | | 7/1991 | Kawamura et al. |
| 5,234,459 A | * | 8/1993 | Lee ............... 606/203 |
| 5,312,431 A | * | 5/1994 | McEwen ........... 606/202 |
| 5,722,397 A | | 3/1998 | Eppstein |
| 5,904,655 A | * | 5/1999 | Brackett .......... 600/490 |
| 6,314,058 B1 | * | 11/2001 | Lee ................. 368/10 |
| 6,491,647 B1 | | 12/2002 | Brigder et al. |
| 6,529,754 B2 | * | 3/2003 | Kondo ............. 600/344 |

(Continued)

FOREIGN PATENT DOCUMENTS

CN    2314735 Y    4/1999

(Continued)

*Primary Examiner*—Charles A. Marmor, II
*Assistant Examiner*—Anita Saidi
(74) *Attorney, Agent, or Firm*—Martin Fleit; Paul D. Bianco; Fleit Gibbons Gutman Bongini & Bianco, PL

(57) ABSTRACT

The present invention provides an automatic blood pressure monitor for measuring the arterial blood pressure at a location on a patient. The automatic monitor of the invention does not require an external pump of any type. The invention uses a propellant supply chamber containing a predetermined quantity of propellant in order to inflate a pressure occluding bladder, thus allowing the measurement to be made. All of the elements comprising the monitor are attached to or are an integral part of a strap, which supports the monitor at the desired location on the patient. The monitor of the invention is inexpensive and simple to operate and can be used by non-professional persons in non-clinical or non-laboratory environments.

20 Claims, 6 Drawing Sheets

U.S. PATENT DOCUMENTS

2002/0084904 A1 * 7/2002 De La Huerga .......... 340/573.1

FOREIGN PATENT DOCUMENTS

| EP | 0348297 | 12/1989 |
| EP | 0465192 | 1/1992 |
| FR | 2469908 | 5/1981 |
| FR | 2599616 | 12/1987 |

* cited by examiner

BLOOD PRESSURE MONITOR

FIELD OF THE INVENTION

The present invention is related to the field of equipment for medical testing and diagnosis. Specifically the present invention relates to automatic blood pressure monitors for making measurements at the arm, wrist and finger. More specifically the present invention relates to automatic blood pressure monitors, which are self contained, do not use an external pump, and can be used by non-professional persons in non-clinical or non-laboratory environments.

BACKGROUND OF THE INVENTION

Automatic home monitoring devices for blood pressure measurements at the arm, wrist, or finger have become available in ever increasing numbers of designs in recent years.

Home monitors are recommended for use by persons who wish to take either periodic or sporadic measurements in order to keep track of the general state of their health especially persons in various groups that are considered potential candidates for developing high blood pressure such as over-weight persons, smokers, and pregnant women. Home monitors are useful to take a series of measurements over a period of time in order to establish a data base for later diagnosis, to monitor drug dosages in order to optimize treatment for controlling high blood pressure, in emergency situations, in cases when it is simply not possible or convenient to visit a doctor or clinic, etc. For many people home monitoring is considered to be the most accurate method for blood pressure measurement because at home these people are relaxed whereas they tend to become nervous in clinical environments causing their blood pressure to rise.

Despite the fact that sales of automatic home monitoring devices increase yearly, only a very small percentage of the persons in the groups mentioned above who should be periodically monitoring their blood pressure actually own such a device. The reasons for this situation are many but the principal ones are cost, reliability over time, and the psychological one that most people normally consider themselves to be healthy and therefore refrain from purchasing medical monitoring devices since such a purchase would be considered to be an admission that perhaps all is not well.

Automatic monitoring devices for blood pressure measurement usually contain the following elements: inflatable cuff; electro-pneumatic unit, mainly comprising a pump and an electric valve to inflate and deflate the cuff; transducer; electronic circuit; digital readout; and power supply, either batteries or connection to mains supply. All of these elements, especially the pump, the electric valve, and the significant power requirements of the pump combine to make the majority of automatic monitors expensive for the average potential user, the relative expense being all the more pronounced for a device that is normally not used frequently. Additionally, inclusion of all of the above elements results in relatively bulky devices and limits the ability of manufacturers to reduce the size of monitors to pocket-size dimensions which can be conveniently carried out of the house on business trips, vacations, etc.

It is therefore a purpose of the present invention to provide an automatic monitoring device for blood pressure measurement that avoids the above-mentioned drawbacks of presently available devices designed for a similar purpose, specifically it is a purpose of the present invention to provide an automatic monitoring device that does not comprise an electro-pneumatic unit to inflate and deflate a cuff.

It is another purpose of the present invention to provide an automatic monitoring device for blood pressure measurement that is significantly less expensive than presently available devices.

It is yet another purpose of the present invention to provide an automatic monitoring device for blood pressure measurement that is significantly smaller than presently available devices.

It is still another purpose of the present invention to provide an automatic monitoring device for blood pressure measurement that is small enough to be carried in the pocket.

It is yet a further purpose of the present invention to provide an automatic monitoring device for blood pressure measurement that can be discarded after a single or a limited number of uses.

It is a further purpose of the present invention to provide an automatic monitoring device for blood pressure measurement that is extremely reliable over its intended life span.

It is a still further purpose of the present invention to provide an automatic monitoring device for blood pressure measurement that is easy to operate.

Further purposes and advantages of this invention will appear as the description proceeds.

SUMMARY OF THE INVENTION

In a first aspect the present invention provides an automatic blood pressure monitor for measuring the arterial blood pressure at a location on a patient. A preferred embodiment of the monitor of the invention comprises:
  a) an inflatable blood flow occluding bladder;
  b) a pressure generator for inflating the blood flow occluding bladder;
  c) means for deflating the blood flow occluding bladder;
  d) means for detecting, computing and producing an output indicative of the pressure in the artery;
  e) means for converting the output into visible signals;
  f) means for displaying the signals;
  g) means for supplying energy to the monitor; and
  h) a strap for supporting the monitor at the location on the patient.

In preferred embodiments, the pressure generator comprises a propellant supply chamber containing a predetermined quantity of propellant and an exit valve for releasing the propellant; the means for deflating the blood flow occluding bladder comprises a permanently open small exit hole of predetermined size in the blood flow occluding bladder; the energy supply means is necessary only for supplying energy for the operation of the detecting, computing, converting, and display means; and all of the elements comprising the monitor are attached to or are an integral part of the strap. The predetermined quantity of propellant, the volume of the flow occluding bladder and the ratio of the cross-sectional area of the opening in the exit valve and the cross-sectional area of the exit hole in the blood flow occluding bladder are such that, upon opening the exit valve the propellant flowing into the blood flow occluding bladder will inflate the blood flow occluding bladder to an initial maximum pressure greater than the pressure necessary to occlude the flow of blood at the location. The pressure in the blood flow occluding chamber decreases from the maximum value, at a predetermined rate, to a value less than the diastolic pressure at the location in the artery as the propellant escapes from the blood flow occluding bladder through the exit hole. In some preferred embodiments of the invention, the automatic blood pressure monitor further comprises an intermediate chamber.

In another preferred embodiment of the invention, the automatic blood pressure monitor for measuring the arterial blood pressure at a location on a patient comprises:

a) a pressurized blood flow occluding bladder;
b) means for depressurizing the blood flow occluding bladder;
c) means for detecting, computing and producing an output indicative of the pressure in the artery;
d) means for converting the output into visible signals;
e) means for displaying the signals;
f) means for supplying energy to the monitor;
g) a strap for supporting the monitor at the location on the patient.

In this embodiment:

the blood flow occluding bladder comprises an inflatable bladder initially containing a predetermined quantity of gas at a predetermined pressure;
the means for depressurizing the blood flow occluding bladder comprise an exit hole of predetermined size, initially closed by a seal;
the energy supply means is necessary only for supplying energy for the operation of the detecting, computing, converting, and display means; and
all of the elements comprising the monitor are attached to or are an integral part of the strap.

When the strap is tightened, thereby pressing the blood flow occluding bladder against the skin above the artery, the pressure against the skin is high enough to occlude the blood flow in the artery. Upon removing the seal, the gas escapes from the blood flow occluding bladder through the exit hole and the pressure in the blood flow occluding bladder decreases at a predetermined rate to a value less than the diastolic pressure at the location in the artery. The pressurized blood flow occluding bladder can be supplied separately from the monitor and can be attached to the monitor for making a single measurement and replaced with another pressurized blood flow occluding bladder for making another measurement.

In all embodiments of the invention, the monitor can be disposable after one or a limited number of measurements and the artery can be located either in the arm, the wrist, or the finger.

In all embodiments of the invention, the strap of the automatic blood pressure monitor can comprise fastening means and a tongue. Some of the elements of the monitor can be located in/on the strap and the remaining elements of the monitor can be located in/on the tongue.

In some embodiments of the invention the strap and fastening means can be detached from the tongue. The strap and fastening means can be disposable after one or a limited number of measurements and the tongue can be attached to another strap and fastening means and reused.

The means for detecting and producing an output indicative of the pressure in the artery can be pressure transducers or miniature microphones. The means for supplying energy to the detecting, computing, converting, and display means can be batteries or pre-charged capacitors.

In some embodiments of the invention the automatic blood pressure monitor may comprise more than one propellant supply chamber. Each of the propellant supply chambers has an independently opening exit valve. The propellant supply chamber can be supplied separately from the monitor and can be attached to the monitor for making one or more measurements and replaced with another gas supply chamber for making more measurements.

In another aspect, a method is provided for measuring blood pressure using the automatic blood pressure monitor of the invention. The method comprises the following steps:

wrapping the strap around the part of the body where the blood pressure is to be measured with the deflated blood flow occluding bladder placed directly on top of the relevant artery;
tightening the strap until it is pressed firmly against the skin and fastening it;
turning on the detecting, computing, converting, and display means;
opening the exit valve thus allowing the propellant in the supply chamber to flow into the blood flow occluding bladder, initially pressurizing the bladder to a high enough pressure to occlude the flow of blood in the artery;
allowing the gas to escape from the bladder through the exit hole, gradually depressurizing the bladder to a pressure lower than the diastolic and reducing the degree of occlusion of the artery;
measuring the blood flow oscillations and pressure with the detecting means as the blood flow occluding bladder is gradually depressurized;
analyzing the signals from the detecting means with the computing and converting means;
digitally displaying the systolic and diastolic pressure and, optionally, the pulse rate on the display means; and
removing the strap from the body after the measurement.

In the embodiments of the automatic blood pressure monitor of the invention comprising an intermediate chamber, the method comprising the following steps:

wrapping the strap around the part of the body where the blood pressure is to be measured with the deflated blood flow occluding bladder placed directly on top of the relevant artery;
tightening the strap until it is pressed firmly against the skin and fastening it;
turning on the detecting, computing, converting, and display means;
allowing a predetermined amount of propellant to flow from said supply chamber into the intermediate chamber;
preventing or restricting the flow of propellant from said supply chamber into said intermediate chamber;
opening the valve between the intermediate chamber and the blood flow occluding chamber thus allowing the propellant in the intermediate chamber to flow into the blood flow occluding bladder, initially pressurizing the bladder to a high enough pressure to occlude the flow of blood in the artery;
allowing the gas to escape from the bladder through the exit hole, gradually depressurizing the bladder to a pressure lower than the diastolic and reducing the degree of occlusion of the artery;
optionally regulating the pressure in the bladder by means of a release valve that opens if a predetermined pressure in the bladder is exceeded;
measuring the blood flow oscillations and pressure with the detecting means as the blood flow occluding bladder is gradually depressurized;
analyzing the signals from the detecting means with the computing and converting means;
digitally displaying the systolic and diastolic pressure and, optionally, the pulse rate on the display means; and
removing the strap from the body after the measurement.

In the embodiments of the automatic blood pressure monitor of the invention comprising an intermediate chamber, the supply chamber can be filled before the monitor is attached to the body. The flow of propellant from the supply chamber into the intermediate chamber can be prevented by use of a valve and the flow of propellant from the supply chamber into the intermediate chamber can be restricted by use of a very small hole between the two chambers. In one embodiment, the valve between the propellant supply chamber and the intermediate chamber can be opened and the valve between the intermediate chamber and the bladder closed (and vice versa) simultaneously by a single action.

In the embodiments of the automatic blood pressure monitor comprising a pressurized blood flow occluding bladder, the method comprises the following steps:

wrapping the strap around the body part where the blood pressure is to be measured with the pressurized blood flow occluding chamber placed directly on top of the relevant artery;

turning on the detecting, converting, and display means;

tightening the strap until the pressurized blood flow occluding chamber is pressed so firmly against the skin that the blood flow in the artery ceases;

fastening the support means;

opening the seal in the blood flow occluding bladder allowing the gas to escape from the bladder through the exit hole in the bladder, gradually depressurizing the bladder and reducing the degree of occlusion of the artery;

measuring the pulse with the detecting means as the blood flow occluding chamber is gradually depressurized;

analyzing the signals from the detecting means with the converting and computing means;

digitally displaying the systolic and diastolic pressure and, optionally, the pulse rate on the display means; and removing the strap from the body after the measurement is completed.

For measuring blood pressure with any of the embodiments of the automatic blood pressure monitor of the invention the artery can be chosen from the group comprising;

brachial artery, for measurement on the arm;

radial artery, for the wrist; and digital artery, for measurement on the index finger.

All the above and other characteristics and advantages of the invention will be further understood through the following illustrative and non-limitative description of preferred embodiments thereof, with reference to the appended drawings.

DETAILED DESCRIPTION OF PREFERRED EMBODIMENTS

In conventional automatic devices for measuring blood pressure, the cuff, which surrounds the limb at the location where the blood is measured, contains an inflatable bladder. The bladder is initially inflated by using the electro-pneumatic unit to pump in air until a high enough pressure is obtained to occlude the flow of blood through the artery. The air is then slowly released from the cuff and the pressure decreases through values of the systolic pressure and the diastolic pressure in the artery.

The present invention accomplishes its goals by eliminating several of the more expensive and sizeable elements found in automatic home monitoring devices for blood pressure measurement that are listed hereinabove. Specifically the device of the invention does not have an electro-pneumatic unit to inflate and deflate the cuff. The device of the invention uses a pressure generator comprised of a propellant supply chamber, which is prefilled with a quantity of suitable propellant such that, upon being released to an inflatable bladder, one or a multitude of measurements can be made. Because of the absence of the electro-pneumatic unit the energy requirements of the device essentially approach zero and therefore expensive and sizeable batteries are not necessary.

Figure 1A:
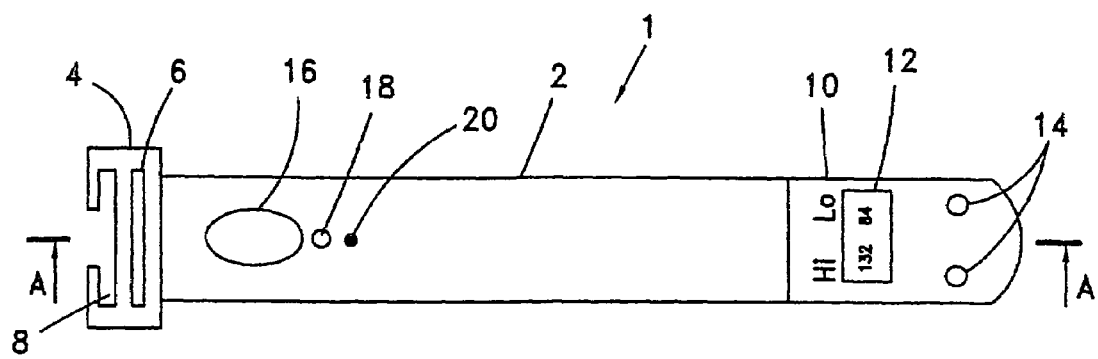
FIGS. 1A, 1B, and 1C schematically show a preferred embodiment of the invention in top, bottom and cross-sectional views respectively.
Figure 1B:
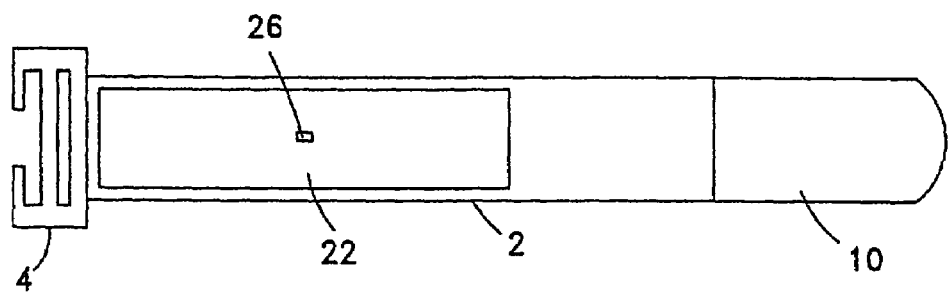
Figure 1C:
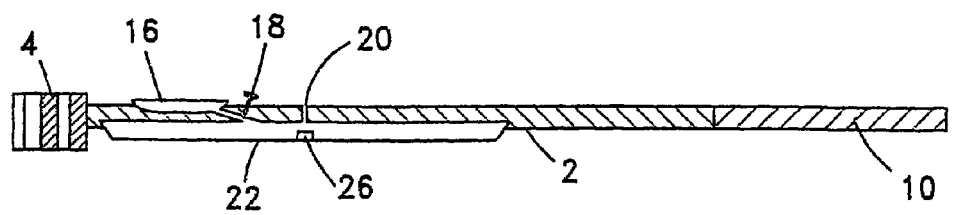

A preferred embodiment of the invention is schematically shown in top, bottom and cross-sectional views respectively in FIGS. 1A, 1B, and 1C. Automatic monitoring device for blood pressure measurement 1 comprises a strap 2, having a buckle 4 at one end, and a tongue 10 at the other end. The strap supports all the elements of the device and is used to attach the device to the body in the appropriate position to make the measurement; the buckle is used to close the strap holding the device firmly against the body during the measurement procedure; and the tongue contains the electronics to process the signals from a transducer and to display the results of the measurements.

It is to be noted that the configuration described with reference to FIGS. 1A to 1C is illustrative and many other configurations can easily be devised. For example, the electronics could be embedded in or attached parts of the strap other than the tongue and the buckle shown can be replaced with any other suitable method for holding the device in place. For convenience, the terms "tongue" and "buckle" are used throughout this specification to designate the electronics unit and fastening arrangement respectively; however, it is to be understood that alternative locations or arrangements are envisaged beyond the literal meaning of these terms. Some of the alternative embodiments will be discussed herein and skilled persons can easily devise others based on the description hereinbelow.

The principle of the invention is best understood with reference to the cross-sectional view. In FIG. 1C it can be seen that two interconnected chambers are created within strap 2. On the external face of the strap (when attached to the body, see the top view, FIG. 1A) is the propellant supply chamber 16. Chamber 16 is prefilled with a propellant that can be a liquefied or compressed gas and is connected to the blood flow occluding bladder 22 on the internal face of strap 2. When valve 18 is opened, the pressure difference between chamber 16 and bladder 22 allows the high pressure gas to escape from chamber 16 and enter and inflate bladder 22. In the case of a liquid propellant, the sudden lowering of the pressure on opening valve 18 causes at least part of the liquid to be transformed into the gaseous state.

The inflated bladder 22 presses against an artery occluding the flow of blood of the person whose blood pressure is being measured. A permanently open small exit hole 20 allows the gas to escape blood flow occluding bladder 22 resulting in deflation of the bladder over a predetermined period of time. During the deflation period, transducer 26 continuously sends signals through wires (not shown in the figures) buried within the strap 2 to the electronics in tongue 10. In FIG. 1C, bladder 22 is shown inflated to illustrate how it protrudes from the strap to press on the artery. When not inflated, bladder 22 is contained within the volume of the strap.

The dimensions of exit hole 20 are significantly smaller than the dimensions of the opening of valve 18. This enables fast inflation of the blood flow occluding bladder 22 (normally less than 1 second) and relatively slow deflation (normally between 15-35 seconds). In addition, the slow outflow from hole 20, which is always open, has an insignificant effect during the inflation stage of bladder 22.

Strap 2 is made of a suitable flexible material, such as polyester or polypropylene. The blood flow occluding bladder 22 is made of material that has much greater elasticity than the material of which the strap is made. This insures that the expansion and contraction of the bladder takes place in a direction roughly orthogonal to the inner face of the strap.

The buckle can be made of any suitable material such as metal or preferably a hard plastic. Any appropriate type of arrangement can be used such as that shown in the figures or any equivalent such as, for example, velcro® fasteners. In the buckle shown in FIGS. 1A to 1C, the tongue is inserted into slot 6 to form a loop around the body part to which the device is to be attached. The strap is tightened as necessary and then looped around hooks 8 to hold the device firmly against the body part. The buckle must enable convenient adjustment of the circumference of the strap to accommodate the different sized limbs of different persons. The tightening of the strap until the device is held firmly against the skin is necessary to enable accurate blood pressure measurement.

The tongue 10 is preferably made of a hard plastic in which is embedded the electronics, including digital display 12, on/off and function selection switches 14, and (not shown in the figures) a dedicated microprocessor or any suitable integrated circuit to process the signals from the transducer, an energy source and other electronic components as required.

The two most common methods used in automatic home automatic blood pressure monitors are the auscultatory and the oscillomteric methods. The auscultatory method is based on the analysis of the sounds emitted by the compression of the artery (first described by Korotkoff in 1905) and the oscillometric method is based on the analysis of the oscillations caused by the arterial pressure pulse.

In preferred embodiments of the invention, the oscillometric method is used to measure the blood pressure and pulse rate. In this method, a miniature pressure transducer 26, located within the blood flow occluding bladder 22 (or in a different chamber interconnected with blood flow occluding bladder 22) placed over the artery detects the pressure changes in the blood flow resulting from the pumping action of the heart. The oscillometric method and the pressure transducers and other electronic elements necessary to carry out the measurements aid calculate and display the results are well known to skilled persons and therefore will not be further discussed herein. In embodiments of the invention that utilize the auscultatory method to measure the blood pressure, a miniature microphone to pick up the sounds in the artery replaces the pressure transducer.

As nonlimiting examples, a Model MPX2300DT1 pressure sensor and accompanying electronics produced by Motorola or a Model 1620 pressure sensor by ICSensors have been found to be suitable for use with the device of the invention.

The device of the invention can employ any suitable propellant, i.e. a liquefied or compressed gas that is not noxious or explosive, such as compressed air or liquid carbon dioxide. The ratio between the volume of the chambers and the maximum pressure to which the blood flow occluding bladder 22 is to be inflated determine the initial pressure in the gas supply chamber. The maximum pressure of bladder 22 should be high enough to occlude flow of blood in the artery; this pressure is normally taken to be about 30 mmHg above the systolic pressure. With conventional automatic home blood pressure monitors the electro-pneumatic unit is actuated until the blood flow ceases in order to accommodate the fact that the systolic pressure varies over a very wide range. Since there is no way of increasing the pressure in the blood flow occluding bladder once the device of the present invention is activated, the initial pressure must be high enough to accommodate all but the most extreme cases. In the preferred embodiments of the invention, the design is based on the requirement that the initial pressure in the bladder 22 upon releasing the gas from propellant supply chamber 16 should be between 220 mmHg to 250 mmHg.

Since it is not necessary to regulate the flow of gas between the chambers, but merely to allow gas to flow between the propellant supply chamber and the blood flow occluding bladder, valve 18 is of a simple and inexpensive design, such as a piston-type valve that is opened and closed by pulling or pushing a piston, or an even simpler design such as a crimped tube that is opened by spreading the walls apart.

The method of using this embodiment of the automatic monitoring device of the invention for blood pressure measurements comprises the following steps:

a) Wrap the strap 2 around the limb where the blood pressure is to be measured with the deflated blood flow occluding bladder 22 placed directly on top of the relevant artery; i.e. a brachial artery for measurement of the arm, radial artery for the wrist and digital artery for measurement on the index finger;

b) Tighten the strap until it is pressed firmly against the skin and fasten it;

c) Turn on the electronics;

d) Open valve 18, allowing the propellant in supply chamber 16 to flow into blood flow occluding bladder 22, initially pressurizing the bladder to a high enough pressure to occlude the flow of blood in the artery;

e) Allow the propellant to escape from bladder 22 through exit hole 20, gradually depressurizing the bladder, to a pressure lower than the diastolic, reducing the degree of occlusion of the artery;

f) Measure the blood flow oscillations and pressure with pressure transducer 26 as blood flow occluding bladder 22 is gradually depressurized, the electronics analyzing the signals from transducer 26 and digitally displaying the systolic and diastolic pressure and, optionally, the pulse rate on the display 12; and g) Remove the strap from the body after the measurement.

As can be appreciated from this description of the measurement procedure, no particular amount of training is necessary and no assistance is needed to carry out the measurements.

The blood pressure measuring device of the invention is resposable, that is it is sufficiently inexpensive that it can be used only once or a limited number of uses and then discarded. In order to even further reduce the cost of the device of the invention, other alternative embodiments are possible.

Figure 2A:
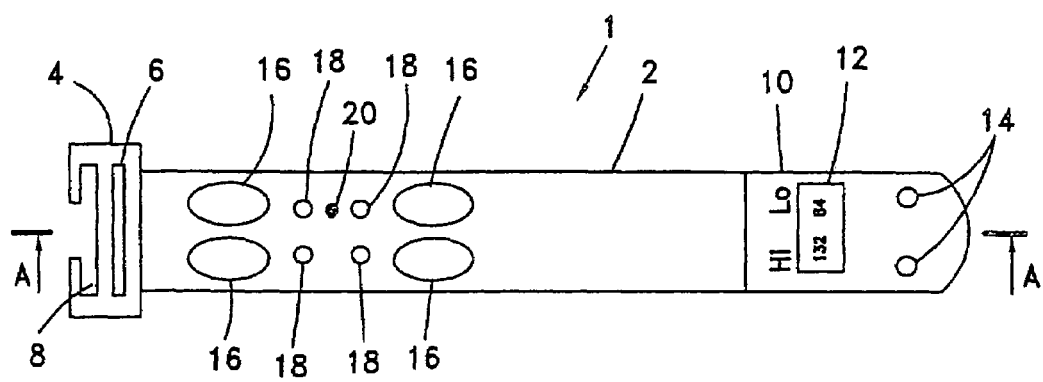
FIGS. 2A to 2C schematically show respectively top, bottom, and cross-sectional views of an embodiment having four independent gas supply chambers.
Figure 2B:
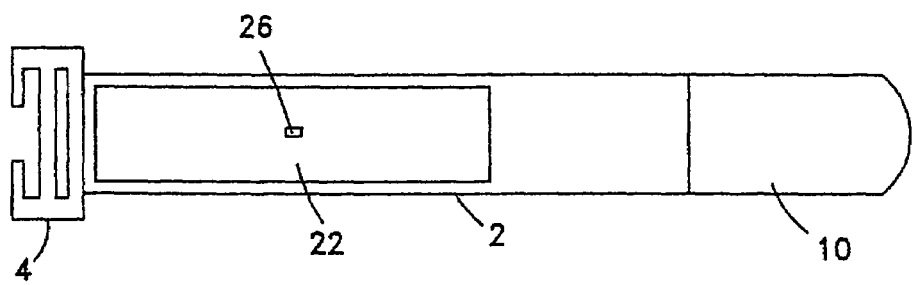
Figure 2C:
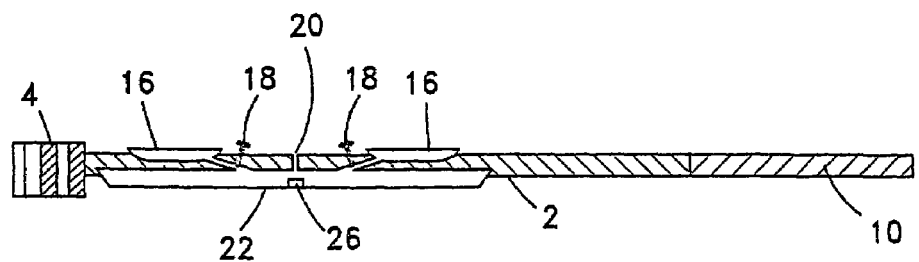

For example, one way of reducing the cost of the device of the invention is to provide more than one chamber 16 containing propellant on the strap, thus allowing multiple measurements to be made with a single device. This variation is especially useful, for example, in cases where a patient must take a series of daily measurements over a short period of time. In this form, the patient obtains a device, which is discarded after all of the chambers 16 are emptied. As a non-limiting example, FIGS. 2A to 2C schematically show respectively top, bottom, and cross-sectional views of an embodiment having four independent supply chambers 16.

Figure 7A:
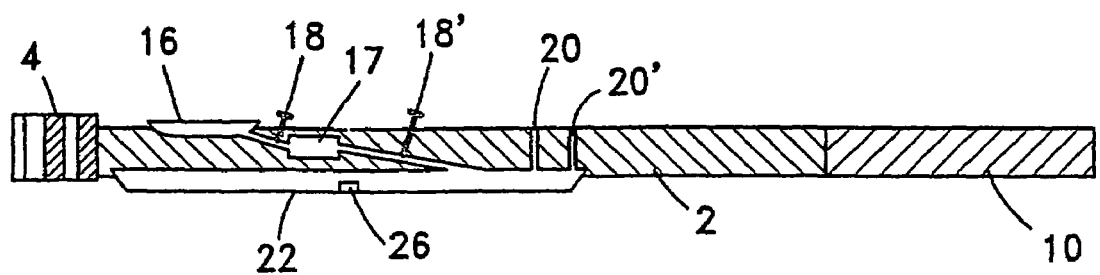
FIGS. 7A and 7B schematically show another embodiment of the invention designed for multiple measurements using a single propellant chamber.
Figure 7B:
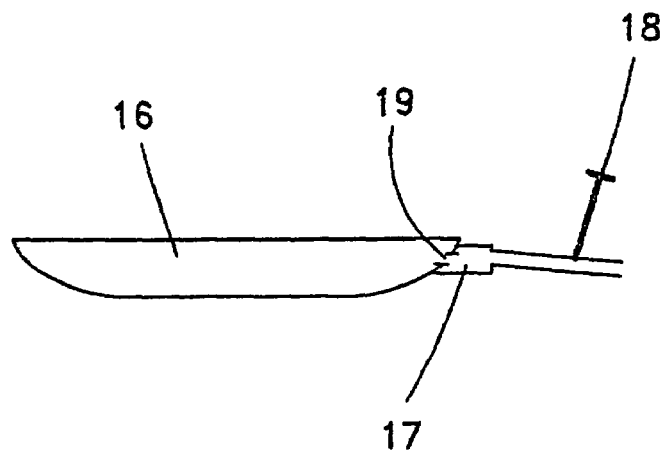

Another embodiment of the invention designed for making multiple measurements using a single propellant chamber is shown in FIGS. 7A and 7B. FIG. 7A is a cross-sectional view from the side, schematically showing this embodiment of the invention. A liquefied gas propellant is stored in supply chamber 16. Also provided in this embodiment is an intermediate chamber 17. With valve 18' closed, valve 18 is opened allowing part of the liquid in chamber 16 to vaporize the resulting gas flowing into chamber 17, when equilibrium is attained, valve 18 is closed and valve 18' opened to allow gas to flow from intermediate chamber 17 into bladder 22 as described hereinabove. In one embodiment of the invention, the two valves 18 and 18' can be mechanically coupled so that a single action, for example pushing on a button on the strap, will simultaneously open one of the valves and close the other, thus additionally simplifying use of the device. The dimensions of intermediate chamber 17 are such that it will contain a quantity of gas sufficient to inflate bladder 22 and carry out the desired measurement. The supply chamber 16 contains enough propellant to repeat this process several times allowing multiple measurements to be made before the device is discarded or a new propellant supply chamber is attached to strap 2.

To prevent over-pressure in bladder 22, which can be the result of high ambient temperature or the transfer of part of the liquid from supply chamber along with the flow of gas into intermediate chamber 17, a release valve 20' can be supplied. Release valve 20' only opens if a predetermined pressure in bladder 22 is exceeded and is of conventional design such as for example a ball and spring arrangement or an elastic orifice. Release valve 20' can be supplied with all other embodiments of the invention if desired.

FIG. 7B schematically shows one of the many alternative ways of implementing this embodiment of the invention. In this embodiment, intermediate chamber 17 is a small antechamber to propellant supply chamber 16. The two are connected by a small permanently opened hole 19. Chamber 16 and chamber 17 are filled with liquid and gas propellant in equilibrium. Hole 19 is very small compared with the cross-sectional area of the passage between chamber 17 and the bladder 22. In this case, upon opening valve 18, the flow of propellant from supply chamber 16 into chamber 17 is so restricted compared to the flow between chamber 17 and the bladder that essentially only the amount of propellant originally contained in chamber 17 is transferred to the bladder. Upon closing valve 18, chamber 17 again fills with propellant and the device is ready for making another measurement.

The propellant supply chamber 16 need not be a chamber created within the strap 2, as described hereinabove, but can be a small container that is permanently attached to the strap for one time use of the device. Alternatively, means can be supplied for temporarily attaching the container of propellant and connecting it to the strap 2 so that it can be replaced with another similar container for repeated use of the device.

Figure 3:
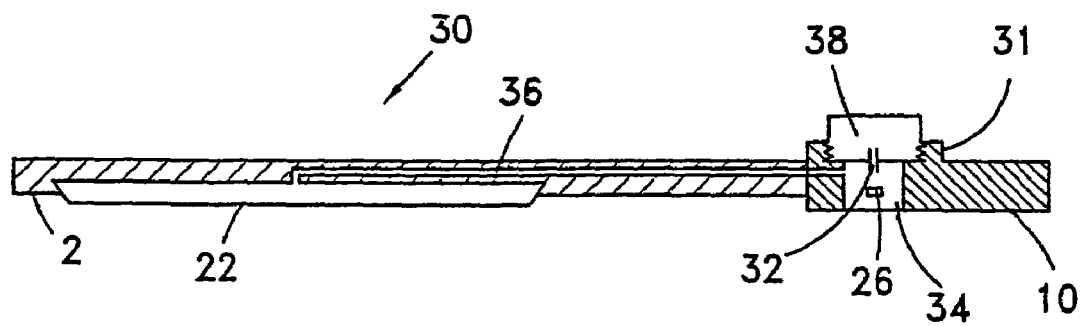
FIG. 3 schematically shows a cross-sectional view of an embodiment comprising a detachable gas supply chamber.

In FIG. 3 is schematically shown a cross-sectional view of an embodiment of the blood pressure measurement device 30 comprising a detachable propellant supply chamber 38. In this embodiment the transducer 26 is placed within a hollow chamber 34 in the rigid tongue 10. Chamber 34 is connected to bladder 22 by means of open passageway 36 in strap 2 and is connected to the gas supply chamber 38 by passage 32. Passage 32 could be a hollow needle that penetrates a gasket in the bottom of chamber 38, releasing the propellant, as the chamber 38 is screwed into a threaded seat 31 on tongue 10.

Figure 4:
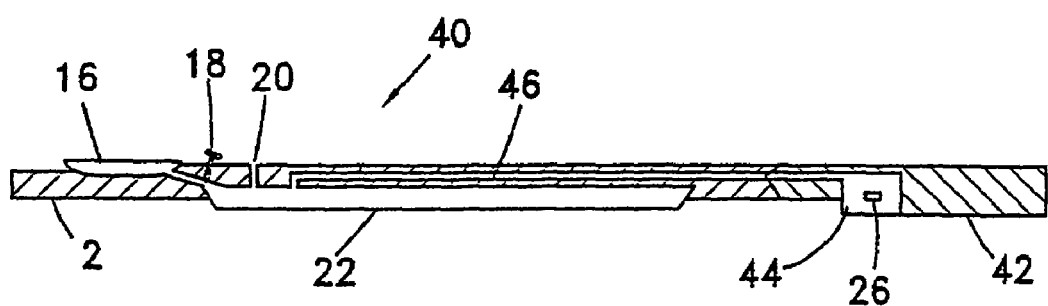
FIG. 4 schematically shows a cross-sectional view of an embodiment comprising a detachable strap.

FIG. 4 schematically shows a cross-sectional view of an embodiment comprising a detachable electronics unit. The electronics unit, including transducer 26 is enclosed in tongue 42, which is detachable from the strap 2. Transducer 26 is located in hollow chamber 44 in the rigid detachable tongue 42. Passage 46 allows free flow of gas from bladder 22 in the strap 2 to chamber 44. A new strap containing the propellant supply chamber 16, valve 18, and blood flow occluding bladder 22 is connected to the tongue 42 containing the electronics unit before each measurement and discarded after each use while the electronics unit can be reused for many measurements.

As mentioned hereinabove, the absence of an electric-pneumatic unit to inflate a cuff results in an extremely low requirement for electrical energy since electricity is only needed to power the electronics during the time of the actual measurement, typically less than half a minute The total energy requirement per measurement is on the order of a few milliwatts. For devices designed for one-time or a limited number of uses, this amount of energy can be supplied by an extremely inexpensive battery built into the device and discarded with it after use. For these devices the energy can be also supplied by pre-charged capacitors that slowly release their stored energy on demand, either in a single or multiple steps as required.

Figure 5A:
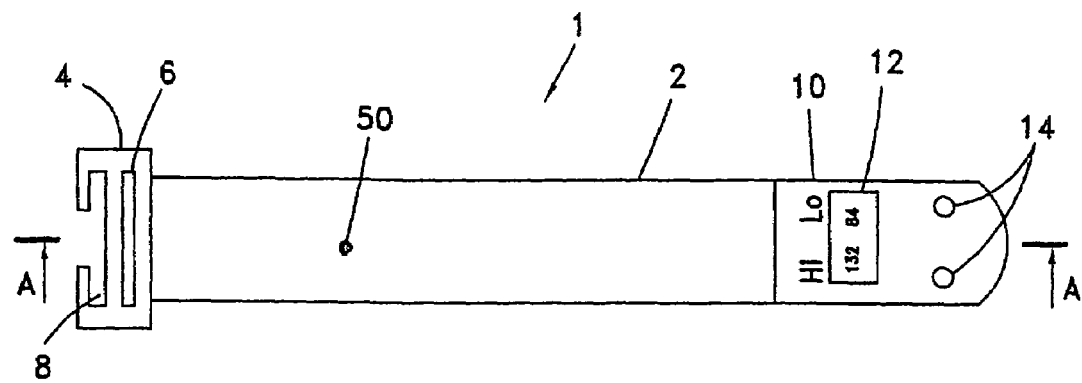
FIGS. 5A to 5C schematically show a simplified embodiment of the automatic monitoring device for blood pressure measurements of the invention in top, bottom, and cross-sectional views respectively.
Figure 5B:
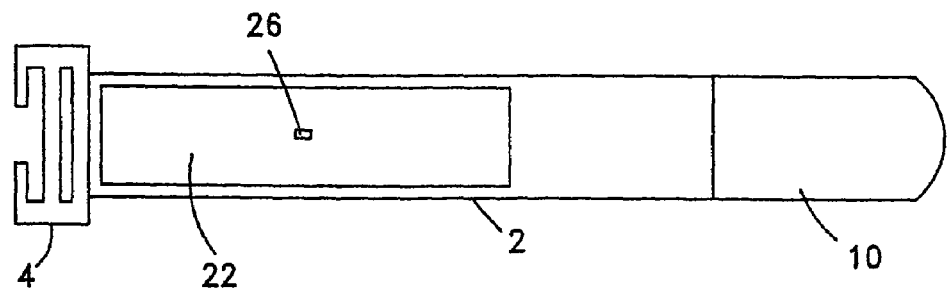
Figure 5C:
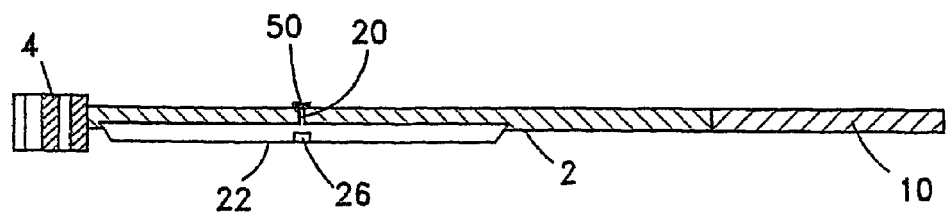

A simplified embodiment of the automatic monitoring device for blood pressure measurements of the invention is schematically shown in top, bottom, and cross-sectional views respectively in FIGS. 5A to 5C.

In this embodiment only one chamber, blood flow occluding chamber 22, is provided on the strap. Chamber 22 is prefilled with compressed gas that is kept inside by seal 50 covering exit hole 20.

The method of using this embodiment of the automatic monitoring device of the invention for blood pressure measurements comprises the following steps:
  a) Wrap the strap 2 around the body part where the blood pressure is to be measured with the pressurized blood flow occluding chamber 22 placed directly on top of the relevant artery;
  b) Turn on the electronics;
  c) Tighten the strap until pressurized blood flow occluding chamber 22 is pressed so firmly against the skin that the blood flow in the artery ceases (indicated on the display);
  d) Fasten the strap;
  e) Open seal 50 allowing the gas to escape from chamber 22 through exit hole 20, gradually depressurizing chamber 22, to a pressure lower than the diastolic, reducing the degree of occlusion of the artery;
  f) Measure the pulse with pressure transducer 26 as blood flow occluding chamber 22 is gradually depressurized, the electronics converting the signals from transducer 26 and digitally displaying the systolic and diastolic pressure and, optionally, the pulse rate on the display 12; and
  g) Remove the strap from the body after the measurement is completed.

In this embodiment, the pressurized blood flow occluding chamber can be an integral part of the strap as described hereinabove in which case either the entire device is discarded after use or the electronics and transducer portion can be separated from the device for reuse with another strap and prefilled chamber. In another variation, only the pressurized blood flow occluding chamber is replaced after each measurement. In this case, the separate chamber is held in place by any suitable means such as slipping the pressurized chamber into a pocket on the inside of the strap or the use of velcro® fasteners;

To get an idea of the size of the device, the blood flow occluding bladder should have width and length that are respectively approximately 40% and 80% of the limb circumference. For an average arm the circumference is 24 to 44 cm, for the wrist 12 to 20 cm for finger the circumference is 5 to 8 cm.

Figure 6:
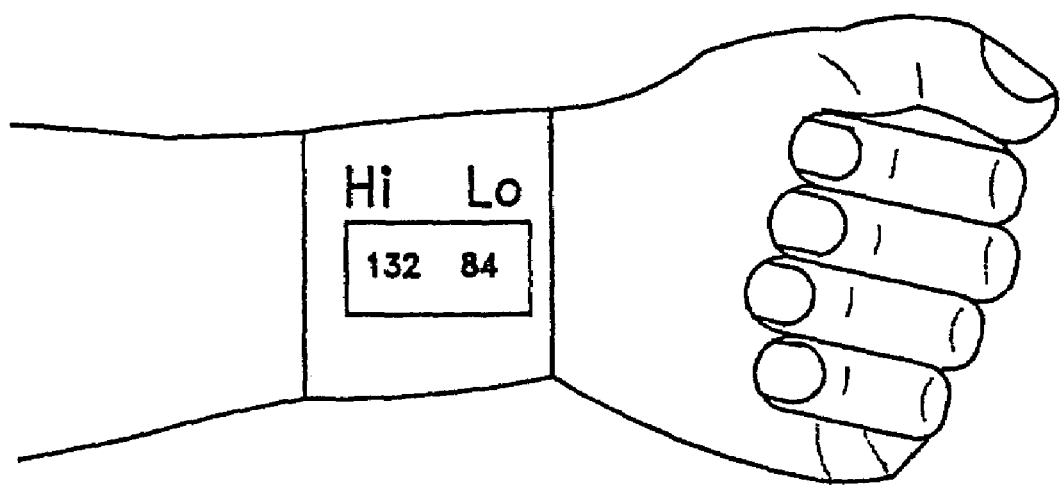
FIG. 6 shows an embodiment of the automatic monitoring device for blood pressure measurements of the invention on the wrist of a person.

FIG. 6 shows an embodiment of the automatic monitoring device for blood pressure measurements of the invention attached to the wrist of a person.

Although embodiments of the invention have been described by way of illustration, it will be understood that the invention may be carried out with many variations, modifications, and adaptations, without departing from its spirit or exceeding the scope of the claims.

The invention claimed is:

1. An automatic blood pressure monitor for measuring the arterial blood pressure at a location on a patient, said monitor comprising:
   a) an inflatable blood flow occluding bladder;
   b) a pressure generator for inflating said blood flow occluding bladder;
   c) means for deflating said blood flow occluding bladder;
   d) means for detecting, computing and producing an output indicative of the pressure in the artery;
   e) means for convening said output into visible signals;
   f) means for displaying said signals;
   g) means for supplying energy to said monitor; and
   h) a strap for supporting said monitor at said location on said patient; characterized in that,
   said pressure generator comprises a propellant supply chamber containing a predetermined quantity of propellant, said chamber having an exit valve for releasing said propellant;
   said means for deflating said blood flow occluding bladder comprises a permanently open small exit hole of predetermined size in said blood flow occluding bladder, said permanently open small exit hole being valve free;
   said energy supply means is necessary only for supplying energy for the operation of said detecting, computing, converting, and display means; and
   all of the elements comprising said monitor are attached to or are an integral pan of said strap;
   whereupon said predetermined quantity of propellant, the volume of said flow occluding bladder and the ratio of the cross-sectional area of the opening in said exit valve and the cross-sectional area of the valve free exit hole in said blood flow occluding bladder are such that, upon opening said exit valve said propellant flowing into said blood flow occluding bladder will inflate said blood flow occluding bladder to an initial maximum pressure greater than the pressure necessary to occlude the flow of blood at said location, said pressure in said blood flow occluding chamber decreasing from said maximum value, at a predetermined rate, to a value less than the diastolic pressure at said location in said artery as said propellant escapes from said blood flow occluding bladder through said exit hole; wherein for at least part of the process for measuring the arterial blood pressure, said propellant is flowing into and out of said blood flow occluding bladder simultaneously.

2. An automatic blood pressure monitor according to claim 1, wherein the artery is located either in the arm, the wrist, or the finger.

3. An automatic blood pressure monitor according to claim 1, wherein the strap comprise fastening means and a tongue; wherein, some of the elements of said monitor are located in/on said strap and the remaining elements of said monitor are located in/on said tongue.

4. An automatic blood pressure monitor according to claim 3, wherein the strap and fastening means can be detached from the tongue.

5. An automatic blood pressure monitor according to claim 4, wherein the strap and fastening means are disposable after one or a limited number of measurements and the tongue is attached to another strap and fastening means and reused.

6. An automatic blood pressure monitor according to claim 1, wherein said monitor is disposable after one or a limited number of measurements.

7. An automatic blood pressure monitor according to claim 1, wherein the means for detecting and producing an output indicative of the pressure in the artery are selected from the group comprising:
   a) pressure transducers; and
   b) miniature microphones.

8. An automatic blood pressure monitor according to claim 1, wherein means for supplying energy to the detecting, computing, converting, and display means are chosen from the group comprising:
   a) batteries; and
   b) pre-charged capacitors.

9. An automatic blood pressure monitor according to claim 1, comprising more than one propellant supply chamber each of said propellant supply chambers having an independently opening exit valve.

10. An automatic blood pressure monitor according to claim 1, wherein the propellant supply chamber is supplied separately from said monitor and can be attached to said monitor for making one or more measurements and replaced with another gas supply chamber for making more measurements.

11. An automatic blood pressure monitor according to claim 1 further comprising an intermediate chamber.

12. A method for measuring arterial blood pressure using the automatic blood pressure monitor of claim 11, said method comprising the following steps:
   wrapping the strap around the part of the body where the blood pressure is to be measured with the deflated blood flow occluding bladder placed directly on top of the relevant artery;
   tightening the strap until it is pressed firmly against the skin and fastening it;
   turning on the detecting, computing, converting, and display means;
   allowing a predetermined amount of propellant to flow from said supply chamber into the intermediate chamber;
   preventing or restricting the flow of propellant from said supply chamber into said intermediate chamber;
   opening the valve between said intermediate chamber and said blood flow occluding bladder thus allowing the propellant in the intermediate chamber to flow into said blood flow occluding bladder, initially pressurizing said bladder to a high enough pressure to occlude the flow of blood in the artery;

allowing said gas to escape from said bladder through the valve free exit hole, gradually depressurizing said bladder to a pressure lower than the diastolic and reducing the degree of occlusion of the artery;

optionally regulating the pressure in said bladder by means of a release valve that opens if a predetermined pressure in said bladder is exceeded;

measuring the blood flow oscillations and pressure with the detecting means as said blood flow occluding bladder is gradually depressurized;

analyzing the signals from said detecting means with said computing and converting means;

digitally displaying the systolic and diastolic pressure and, optionally, the pulse rate on said display means; and removing said swap from the body after the measurement; wherein for at least part of the process for measuring the arterial blood pressure, said propellant is flowing into and out of said blood flow occluding bladder simultaneously.

13. A method according to claim 12, wherein the step of allowing a predetermined amount of propellant to flow from the supply chamber into the intermediate chamber takes place before the strap is wrapped around the part of the body.

14. A method according to claim 12, wherein preventing the flow of propellant from the supply chamber into the intermediate chamber is implemented by use of a valve and restricting the flow of propellant from said supply chamber into said intermediate chamber is implemented by use of a very small hole between said supply chamber into said intermediate chamber.

15. A method according to claim 12, wherein the step of preventing the flow of propellant from the supply chamber into the intermediate chamber and the step of opening the valve between said intermediate chamber and the blood flow occluding bladder are implemented simultaneously by a single action.

16. A method for measuring arterial blood pressure using the automatic blood pressure monitor of claim 1, said method comprising the following steps:

wrapping the strap around the part of the body where the blood pressure is to be measured with the deflated blood flow occluding bladder placed directly on top of the relevant artery;

tightening the strap until it is pressed firmly against the skin and fastening it;

turning on the detecting, computing, convening, and display means;

opening the exit valve thus allowing the propellant in the supply chamber to flow into said blood flow occluding bladder, initially pressurizing said bladder to a high enough pressure to occlude the flow of blood in the artery;

allowing said gas to escape from said bladder through the valve free exit hole, gradually depressurizing said bladder to a pressure lower than the diastolic and reducing the degree of occlusion of the artery;

measuring the blood flow oscillations and pressure with the detecting means as said blood flow occluding bladder is gradually depressurized;

analyzing the signals from said detecting means with said computing and converting means;

digitally displaying the systolic and diastolic pressure and, optionally, the pulse rate on said display means; and removing said strap from the body after the measurement; wherein for at least part of the process of measuring the blood pressure, said propellant is flowing into and out of said blood flow occluding bladder simultaneously.

17. A method for measuring arterial blood pressure according to claim 16, wherein the artery is chosen from the group comprising;
brachial artery, for measurement on the arm;
radial artery, for the wrist; and
digital artery, for measurement on the index finger.

18. An automatic blood pressure monitor for measuring the arterial blood pressure at a location on a patient, said monitor comprising:
a) a pressurized blood flow occluding bladder;
b) means for depressurizing said blood flow occluding bladder;
c) means for detecting, computing and producing an output indicative of the pressure in the artery;
d) means for converting said output into visible signals;
e) means for displaying said signals;
f) means for supplying energy to said monitor;
g) a strap for supporting said monitor at said location on said patient; characterized in that, said blood flow occluding bladder comprises an inflatable bladder initially containing a predetermined quantity of gas at a predetermined pressure;

said means for depressurizing said blood flow occluding bladder comprise an exit hole of predetermined size, initially closed by a seal said exit hole of predetermined size being valve free;

said energy supply means is necessary only for supplying energy for the operation of said detecting, computing, converting, and display means; and all of the elements comprising said monitor are attached to or are an integral part of said strap;

whereupon, on tightening said swap, thereby pressing said blood flow occluding bladder against the skin above said artery, the pressure against the skin is high enough to occlude the blood flow in said artery and upon removing said seal, said pressure in said blood flow occluding bladder decreases at a predetermined rate to a value less than the diastolic pressure at said location in said artery as said gas escapes from said blood flow occluding bladder though said valve free exit hole.

19. An automatic blood pressure monitor according to claim 18, wherein the pressurized blood flow occluding bladder is supplied separately from said monitor and can be attached to said monitor for making a single measurement and replaced with another pressurized blood flow occluding bladder for making another measurement.

20. A method for measuring arterial blood pressure using the automatic blood pressure monitor of claim 18, said method comprising the following steps:

wrapping the strap around the body part where the blood pressure is to be measured with the pressurized blood flow occluding chamber placed directly on top of the relevant artery;

turning on the detecting, converting, and display means;

tightening the strap until said pressurized blood flow occluding chamber is pressed so firmly against the skin that the blood flow in said artery ceases;

fastening said support means;

opening the seal in the blood flow occluding bladder allowing the gas to escape from said bladder through the valve free exit hole in said bladder, gradually depressurizing said bladder and reducing the degree of occlusion of said artery;

measuring the pulse with said detecting means as said blood flow occluding chamber is gradually depressurized;

analyzing the signals from said detecting means with said converting and computing means;

digitally displaying the systolic and diastolic pressure and, optionally, the pulse rate on said display means; and removing said strap from the body after the measurement is completed.

* * * * *